United States Patent [19]

Pepper et al.

[11] Patent Number: 5,144,024

[45] Date of Patent: Sep. 1, 1992

[54] SHELF STABLE LIQUID XYLITOL COMPOSITIONS

[76] Inventors: Tammy Pepper, 38 Napoleon Road, St. Margarets, Twickenham, Middlesex TW1 3EP, Great Britain; Pasi Keipinen, Jokitormanpolku 6, SF-48400 Kotka, Finland

[21] Appl. No.: 596,064

[22] Filed: Oct. 11, 1990

[51] Int. Cl.$^5$ .................. C13F 1/02; C07H 1/08; A23G 3/00
[52] U.S. Cl. ................... 536/128; 426/658; 127/58
[58] Field of Search ........ 426/658, 659, 660; 536/128, 18.6; 127/58; 568/872

[56] References Cited

U.S. PATENT DOCUMENTS

| | | | |
|---|---|---|---|
| 3,980,719 | 9/1976 | Buckl | 568/872 |
| 4,008,285 | 2/1977 | Melaja | 568/872 |
| 4,066,711 | 1/1978 | Melaja | 568/872 |
| 4,246,431 | 1/1981 | Munir | 568/872 |
| 4,828,845 | 5/1989 | Zamudio-Tena | 426/5 |
| 4,911,937 | 3/1990 | Crosello | 426/103 |
| 4,917,916 | 4/1990 | Hirao | 426/658 |
| 4,959,225 | 9/1990 | Wong | 426/3 |
| 4,961,941 | 10/1990 | Cocco | 426/94 |
| 4,961,942 | 10/1990 | Cocco | 426/94 |

FOREIGN PATENT DOCUMENTS 1401590 7/1975 United Kingdom.
1559989 1/1980 United Kingdom.

OTHER PUBLICATIONS

Melida technical information.
Kirk-Othmer Encyclopedia of Chemical Technology, 1978, 3rd ed., vol. 1, John Wiley & Sons, N.Y., pp. 765-766.
The Merck Index 10th ed., Merck & Co. Rahway, N.J., 1983, #9894, 8569, 5569, 4347.

Primary Examiner—Ronald W. Griffin
Assistant Examiner—Ralph G. Tomer
Attorney, Agent, or Firm—Kenyon & Kenyon

[57] ABSTRACT

A shelf-stable liquid xylitol product, a method for its production, and means for its use are disclosed.

22 Claims, 1 Drawing Sheet

SHELF STABLE LIQUID XYLITOL COMPOSITIONS

BACKGROUND OF THE INVENTION

The link between ordinary sugar (sucrose) consumption and the occurrence of dental caries has been well established. As a result, a considerable amount of research has been directed toward the development of alternative sweetening systems that do not promote tooth decay. At present, the noncariogenic sweetener of choice in commercial applications is sorbitol In most cosmetic applications, such as toothpaste, technical grade liquid sorbitol is used. It contains about 70% dry solids, with at least 70% of the dry solids (50-60% of the total weight) being sorbitol. Because sorbitol at a concentration of more than 70% of the solids has a tendency to crystallize, the remaining portion of most liquid sorbitol products is a mixture of other polyols which prevent such crystallization.

Although sorbitol is, as described above, widely used, it does have some drawbacks. It has only about 60% the sweetness of sucrose. In addition, there is some evidence to suggest that frequent exposure to sorbitol may result in increased acid production in dental plaque and an increased number of sorbitol fermenting organisms within the mouth.

Reports of recent studies in which the sugar alcohol xylitol was compared to sorbitol for use as a sweetener indicate that xylitol may provide several advantages. Xylitol has been found to significantly reduce the frequency of dental caries. Thus, rather than being non-cariogenic like sorbitol, xylitol is actually cariostatic. Furthermore, xylitol's cariostatic properties are observed even when xylitol is used in conjunction with a sweetener that has cariogenic potential. In addition xylitol reduces the development of plaque. It has also been observed that xylitol reacts synergistically with fluoride. In addition, xylitol has the same sweetness as sucrose. Finally, xylitol has humectant properties that have lead to its suggested use in products such as toothpaste, where it prevents plugging of uncapped tubes. See UK Patent 1 559 989, issued to Glas and Ahlgren.

Despite suggestions in the literature that xylitol could provide valuable properties to cosmetic products, its use has been limited for several reasons. Predominantly, it has not, to date, been made available in a form that makes it shelf stable and easy to add into various formulations. Furthermore its manufacturing costs have hindered its substitution for less costly sugar alcohols.

It is therefore the object of this invention to provide a less expensive, technical grade liquid xylitol product. It is a further object of this invention to provide a liquid xylitol product which does not crystallize under normal storage conditions of concentration, time and temperature. Another object of the invention is to provide a liquid xylitol product that is as similar as possible to liquid sorbitol products, thus enabling manufacturers to readily reformulate existing products with a xylitol sweetener.

SUMMARY OF THE INVENTION

These and other objectives are achieved by the invention disclosed herein, wherein a process for the production of a shelf-stable, technical grade liquid xylitol product is disclosed. The resultant product has a total dry solids content ranging from 50-80%. The preferred range is 60-70%. The product contains xylitol at a level of 50-90% of the dry solids, preferably between 60 and 80%. The remainder of the liquid product consists of other polyols, such as sorbitol, maltitol, mannitol or glycerol. In a preferred embodiment, xylitol run-off, at about 70% dry solids (xylitol forms 80-90% of the dry solids) is obtained after a second crystallization stage during the manufacture of crystalline xylitol. This run-off is mixed with maltitol or other polyol syrup to achieve the desired carbohydrate composition. Alternatively, a solution of pure or substantially pure xylitol can be mixed with other polyols such as sorbitol or maltiitol. This avoids the more unusual polyols which are present in the xylitol run-off.

DETAILED DESCRIPTION OF THE INVENTION

Figure 1:
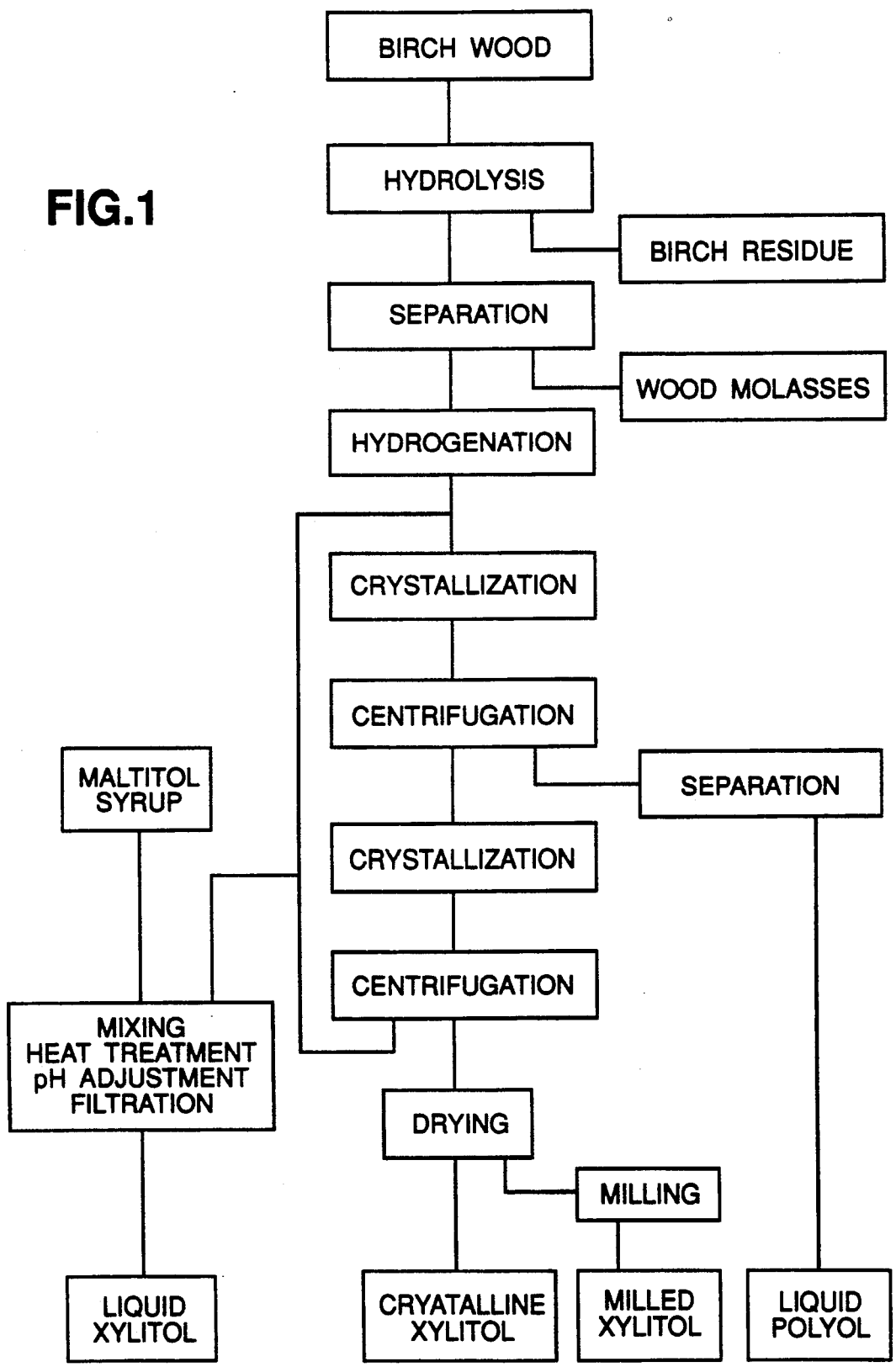

A liquid xylitol composition that is optimum is one which will have a solids content high enough that it will not support the growth of microorganisms, yet low enough to avoid crystallization at usual storage temperatures. The product produced according to the present invention provides these advantages. According to the invention, the liquid xylitol contains 60-80% dry solids, in which xylitol accounts for about 50-90% of the dry solids. Other polyols, which are added singly or in combination as pure solutions or in the form of syrups, comprise about 10-50% of the dry solids. Reducing sugars account for less than about 1% of the dry solids of the composition. In a preferred composition, xylitol accounts for 60-80% of the dry solids, whereas other polyols account for the remaining 20-40% of the dry solids.

Because it if often important to minimize the cost of the liquid xylitol composition, the invention disclosed herein contemplates the use of a xylitol stream taken from an intermediate stage in the xylitol crystallization process. Such a stream would have both a high xylitol content as well as additional polyols that could provide valuable properties to the liquid xylitol composition. A commercial xylitol production scheme is shown in FIG. 1. Typically, wood is hydrolyzed, the residue is separated out, and the remaining hydrolysate is hydrogenated, followed by a series of stages in which xylitol is crystallized and separated out by centrifugation. After two such crystallization and centrifugation steps, the "run-off", which is the remaining liquid containing non-crystallized xylitol as well as other polyols, typically contains about 70% dry solids, 80-90% of which is xylitol. Table 1 below sets forth the typical composition of xylitol run-off.

TABLE 1

| COMPOSITION OF XYLITOL RUN-OFF (% of dry substance) | |
|---|---|
|  | Range |
| Xylitol | 70-98 |
| Sorbitol | 1-10 |
| Galactitol | 0-5 |
| Arabinitol & Rhamnitol | 0-5 |
| Mannitol | 0-2 |
| Others | 1-15 |

This run-off, if used alone, would be stable to microbial fermentation because of its solids content, but it would be prone to crystallization. Such crystallization is avoided, however, by mixing with the run-off an additional polyol, such as maltitol. Preferably the polyol is added so as to account for 20-40% of the dry solids.

The composition of a typical liquid xylitol composition produced according to a preferred embodiment is shown below in Table 2.

TABLE 2

COMPOSITION OF LIQUID XYLITOL*
% of dry substance

| | |
|---|---|
| Xylitol | 60–80 |
| Maltitol | 1–35 |
| Maltotriitol | 0–10 |
| Sorbitol | 3–10 |
| Galactitol | 0–4 |
| Arabinitol & Rhamnitol | 0–4 |
| Mannitol | 0–1 |
| DP4 – DP20+ | 0–5 |
| Other polyols | 0–10 |

*Maltitol syrup used as added polyol

In another embodiment, liquid xylitol is prepared by mixing a solution of pure xylitol with a solution containing other polyols. Although such a method is more costly, it avoids the more unusual polyols contained in the xylitol run-off. According to this embodiment, a xylitol solution is mixed with a solution containing another polyol or mixture of polyols to create a composition containing 60–70% dry solids, 50–90% of which are xylitol, and 10–50% of which are an additional polyol such as maltitol or sorbitol. The xylitol used may be obtained by dissolving crystalline xylitol. Alternatively, substantially pure xylitol produced by hydrogenation of crystalline xylose may be used. Similarly, the non-xylitol polyols are added either in the form of pure solutions or in the form of syrups. The non-xylitol polyols may be used singly or in combination.

The non-xylitol polyols contemplated by the present invention include the sugar alcohols sorbitol, maltitol, mannitol, glycerol, and polyols present in xylitol run-off, including various mixtures or combinations thereof. Such polyols can be obtained by dissolving the crystalline form to produce a pure solution. Alternatively, syrups containing the various sugar alcohols can be utilized. For instance, commercially available sorbitol syrup, wherein sorbitol comprises about 70 to about 100% of the dry solids, or maltitol syrup, wherein maltitol forms approximately 50–95% of the dry solids, can be used. Suitable maltitol syrups that are commercially available include Hystar, Lycasin, Maltisorb and Malbit.

EXAMPLES

Example 1

Liquid xylitol solutions were formulated with dry solids contents ranging from 50–70%. The xylitol in each solution was derived from pure crystals. The xylitol solutions were stored at 5°, 10°, 20°, 25° and 30° C. and monitored for the number of days (d), weeks (w) or months (m) that they were stable to crystal formation (C). The results are shown in Table 3.

TABLE 3

STABILITY OF PURE XYLITOL SOLUTIONS

| % X | % DS | 5° C. C | 10° C. C | 20° C. C | 25° C. C | 30° C. C |
|---|---|---|---|---|---|---|
| 100 | 50 | — | — | — | — | — |
| 100 | 60 | 2w | 1m | — | — | — |
| 100 | 70 | 2w | 2w | 2w | 2w | 2w |

% X = % Xylitol (dry basis)
% DS = % dry solids

These results indicate that pure xylitol solutions exhibit a poor non-crystallizing ability at dry solids levels of 70%, which is the usual concentration of technical grade commercial polyol solutions. At below ambient temperatures (5° and 10° C.), xylitol solutions crystallize at 60% dry solids.

Example 2

Liquid xylitol compositions were formulated with dry solids contents ranging from 55 to 70%, with xylitol concentrations (dry basis) of either 70 or 80%. The xylitol was derived from pure crystals. In addition to xylitol, each composition contained sorbitol derived from Sorbitol LT, a sorbitol syrup in which sorbitol forms approximately 70% of the dry solids. The compositions were stored at temperatures of 5°, 10°, 20°, 25°, 25° and 30° C. and monitored for the number of days (d), weeks (w) or months (m) that they were stable to crystallization (C). The results are shown in Table 4.

TABLE 4

STABILITY OF PURE XYLITOL/SORBITOL FORMULATIONS

| % X | % DS | 5° C. C | 10° C. C | 20° C. C | 25° C. C | 30° C. C |
|---|---|---|---|---|---|---|
| 80 | 55 | — | — | — | — | — |
| 80 | 60 | — | — | — | — | — |
| 80 | 65 | 2w | 2w | — | — | — |
| 80 | 70 | 2w | 2w | — | — | — |
| 70 | 60 | — | — | — | — | — |
| 70 | 70 | 2w | 2w | — | — | — |

These data indicate that the addition of sorbitol to xylitol solutions prevents crystallization at ambient temperatures in solutions containing 70% dry solids.

Example 3

Liquid xylitol compositions were formulated with dry solids contents ranging from 50–70%, with xylitol concentrations (dry basis) of 70 to 90%. The xylitol was derived from pure crystals. In addition to xylitol, each composition contained maltitol derived from Finmalt, a maltitol syrup in which maltitol forms 62 to 70% of the dry solids. The compositions were stored at temperatures of 5°, 10°, 20°, 25° and 30° C. and monitored for the number of days (d), weeks (w), or months (m) that they were stable to crystallization (C). The results are shown in Table 5.

TABLE 5

STABILITY OF PURE XYLITOL/MALTITOL FORMULATIONS

| % X | % DS | 5° C. C | 10° C. C | 20° C. C | 25° C. C | 30° C. C |
|---|---|---|---|---|---|---|
| 90 | 50 | — | — | — | — | — |
| 90 | 70 | — | — | — | — | — |
| 80 | 55 | — | — | — | — | — |
| 80 | 60 | — | — | — | — | — |
| 80 | 65 | — | — | — | — | — |
| 70 | 60 | — | — | — | — | — |
| 70 | 70 | 2w | 2w | — | — | — |

These results indicate that the addition of maltitol to pure xylitol solutions prevents crystallization at ambient temperatures.

Example 4

Liquid xylitol compositions were formulated with dry solids contents of either 60 or 70%, with xylitol concentrations of 70% dry basis. The xylitol was derived from run-off. Sorbitol was added to the compositions by adding sorbitol LT. The compositions were stored at temperatures of 5°, 10°, 20°, 25° and 30° C. and monitored for the number of days (d), weeks (w), or months (m) that they were stable to crystallization (C). The results are shown in Table 6.

TABLE 6

STABILITY OF XYLITOL RUN-OFF/SORBITOL FORMULATIONS

| % X | % DS | 5° C. C | 10° C. C | 20° C. C | 25° C. C | 30° C. C |
|---|---|---|---|---|---|---|
| 70 | 60 | — | — | — | — | — |
| 70 | 70 | 2w | 2w | 2m | 2m | 2m |

These data indicate that xylitol run-off/sorbitol solutions can be produced that have increased stability at ambient temperatures as compared to pure xylitol solutions.

Example 5

Liquid xylitol compositions were formulated with dry solids contents ranging from 55 to 75%, with xylitol concentrations ranging from 50% to 80% dry basis. The xylitol was derived from run-off. Each of the compositions also contained maltitol (from Finmalt). The compositions were stored at temperatures of 5°, 10°, 20°, 25° and 30° C. and monitored for the number of days (d), weeks (w) or months (m) that they were stable to crystallization (C). The results are shown in Table 7.

TABLE 7

STABILITY OF XYLITOL RUN-OFF/MALTITOL FORMULATIONS

| % X | % DS | 5° C. C | 10° C. C | 20° C. C | 25° C. C | 30° C. C |
|---|---|---|---|---|---|---|
| 80 | 55 | — | — | — | — | — |
| 80 | 60 | 2w | 2w | — | — | — |
| 80 | 65 | 2w | 2w | — | — | — |
| 80 | 70 | 2w | 2w | 1m | 2m | 2m |
| 80 | 75 | 1d | 1d | 1w | 1w | 1m |
| 70 | 60 | 2w | 2m | — | — | — |
| 70 | 70 | 2w | 2w | 2m | 2m | 2m |
| 60 | 60 | — | — | — | — | — |
| 60 | 70 | 1m | — | — | — | — |
| 50 | 60 | — | — | — | — | — |
| 50 | 70 | — | — | — | — | — |

These data indicate that the addition of maltitol syrup to xylitol run-off prevents or significantly diminishes crystallization at normal storage temperatures.

Based on the storage tests of the compositions as set forth in Examples 1 through 5, it has been found that xylitol rich compositions with either a non-crystallizing character or a significantly improved non-crystallizing character can be obtained with total dry substance concentrations of about 50% to about 80% by weight dry solids, wherein xylitol comprises between about 50 to about 90% of the dry solids in the composition.

Many obvious variations of the invention disclosed will suggest themselves to those skilled in the art. Nothing in the preceding specification is intended, however, to limit the scope of the invention as defined by the following claims.

We claim:

1. A non-crystallizing liquid xylitol composition having a dry solids content of 60-80%, wherein said dry solids are comprised of 50-90% xylitol and 10-50% non-xylitol monomeric or dimeric polyols.

2. The liquid xylitol composition of claim 1, wherein said dry solids are comprised of 60-80% xylitol and 20-40% non-xylitol monomeric or dimeric polyols.

3. The liquid xylitol composition of claim 1, wherein said non-xylitol polyols are selected from the group consisting of maltitol, sorbitol, mannitol, glycerol and mixtures thereof.

4. The liquid xylitol composition of claim 3 wherein the source of said non-xylitol polyols is pure crystalline solutions.

5. The liquid xylitol composition of claim 3 wherein the source of said non-xylitol polyols is polyol syrups.

6. The liquid xylitol composition of claim 1, wherein said xylitol is derived from run-off from a xylitol crystallization process.

7. The liquid xylitol composition of claim 6, wherein said xylitol and a portion of said non-xylitol polyols are derived from runoff from a xylitol crystallization process, said runoff comprising, on a dry solids basis, approximately 70-98% xylitol, about 1-10% sorbitol, about 0-5% galactitol, about 0-5% arabinitol and rhamnitol and about 0-2% mannitol.

8. The liquid xylitol composition of claim 7, wherein said runoff comprises 80-90% xylitol.

9. The liquid xylitol composition of claim 6 wherein said dry solids content is 70% and said dry solids are comprised of about 50 to about 60% xylitol.

10. A method for producing non-crystallizing liquid xylitol comprising collecting run-off after the second crystallization stage of a xylitol crystallization process, said runoff comprising, on a dry solids basis, approximately 70-98% xylitol, about 1-10% sorbitol, about 0-5% galactitol, about 0-5% arabinitol and rhamnitol and about 0-2% mannitol; adding to said run-off a polyol solution to create a 50-80% dry solids xylitol composition, such that 50-90% of the dry solids of said composition are comprised of xylitol and 10-50% of the dry solids are comprised of non-xylitol polyols.

11. A method according to claim 10 wherein said xylitol run-off comprises 80-90% xylitol.

12. A method according to claim 10 wherein said non-xylitol polyols are selected from the group consisting of sorbitol, maltitol, mannitol, glycerol and mixtures thereof.

13. A method according to claim 12 wherein said non-xylitol polyols are added in the form of one or more polyol syrups.

14. A method according to claim 12 wherein said non-xylitol polyols are added in the form of solutions prepared by dissolving the crystalline form of one or more of said polyols in a solvent.

15. A method for producing a non-crystallizing liquid xylitol composition comprising adding to a xylitol solution one or more non-xylitol polyols to create a composition having 60-80% dry solids, wherein 50-90% of the dry solids are comprised of xylitol and 10-50% of the dry solids are comprised of one or more non-xylitol polyols.

16. The method according to claim 15 wherein said xylitol solution is produced by dissolving crystalline xylitol.

17. The method according to claim 15 wherein said xylitol solution is produced by hydrogenation of crystalline xylose.

18. The method according to claim 15 wherein said xylitol is derived from run-off from a xylitol crystallization process, said runoff comprising, on a dry solids basis, approximately 70-98% xylitol, about 1-10% sorbitol, about 0-5% galactitol, about 0-5% arabinitol and rhamnitol and about 0-2% mannitol.

19. The method according to claim 15 wherein said non-xylitol polyols are derived from run-off from a xylitol crystallization process.

20. The method according to claim 15 wherein said non-xylitol polyols are selected from the group consisting of sorbitol, maltitol, mannitol, glycerol and mixtures thereof.

21. The method according to claim 20 wherein said non-xylitol polyols are derived from one or more polyol syrups.

22. The method according to claim 20 wherein said non-xylitol polyols are added in the form of solutions prepared by dissolving the crystalline form of one or more of said polyols in a solvent.

* * * * *